US00PP36064P3

(12) United States Plant Patent
Kim

(10) Patent No.: US PP36,064 P3
(45) Date of Patent: Aug. 6, 2024

(54) ***STOKESIA* PLANT NAMED 'STAM01'**

(50) Latin Name: *Stokesia laevis*
Varietal Denomination: STAM01

(71) Applicant: Seoha Plant Breeding Institute, Gwangju-si (KR)

(72) Inventor: Kyung-Sook Kim, Gwangju-si (KR)

(73) Assignee: SEOHA Plant Breeding Institute (KR)

( * ) Notice: Subject to any disclaimer, the term of this patent is extended or adjusted under 35 U.S.C. 154(b) by 0 days.

(21) Appl. No.: 18/243,863

(22) Filed: Sep. 8, 2023

(65) Prior Publication Data

US 2024/0114814 P1 Apr. 4, 2024

(51) Int. Cl.
*A01H 5/02* (2018.01)
*A01H 6/14* (2018.01)

(52) U.S. Cl.
USPC ..... Plt./484
CPC ..... *A01H 6/14* (2018.05)

(58) Field of Classification Search
USPC ..... Plt./484
See application file for complete search history.

*Primary Examiner* — Susan McCormick Ewoldt
(74) *Attorney, Agent, or Firm* — Cassandra Bright

(57) ABSTRACT

A new and distinct cultivar of *Stokesia* plant named 'STAM01' is disclosed, characterized by floriferous plants with strong stems and dense foliage. Flowers are large. The new variety is a *Stokesia*, suitable for outdoor garden and container uses.

2 Drawing Sheets

Figure 1:
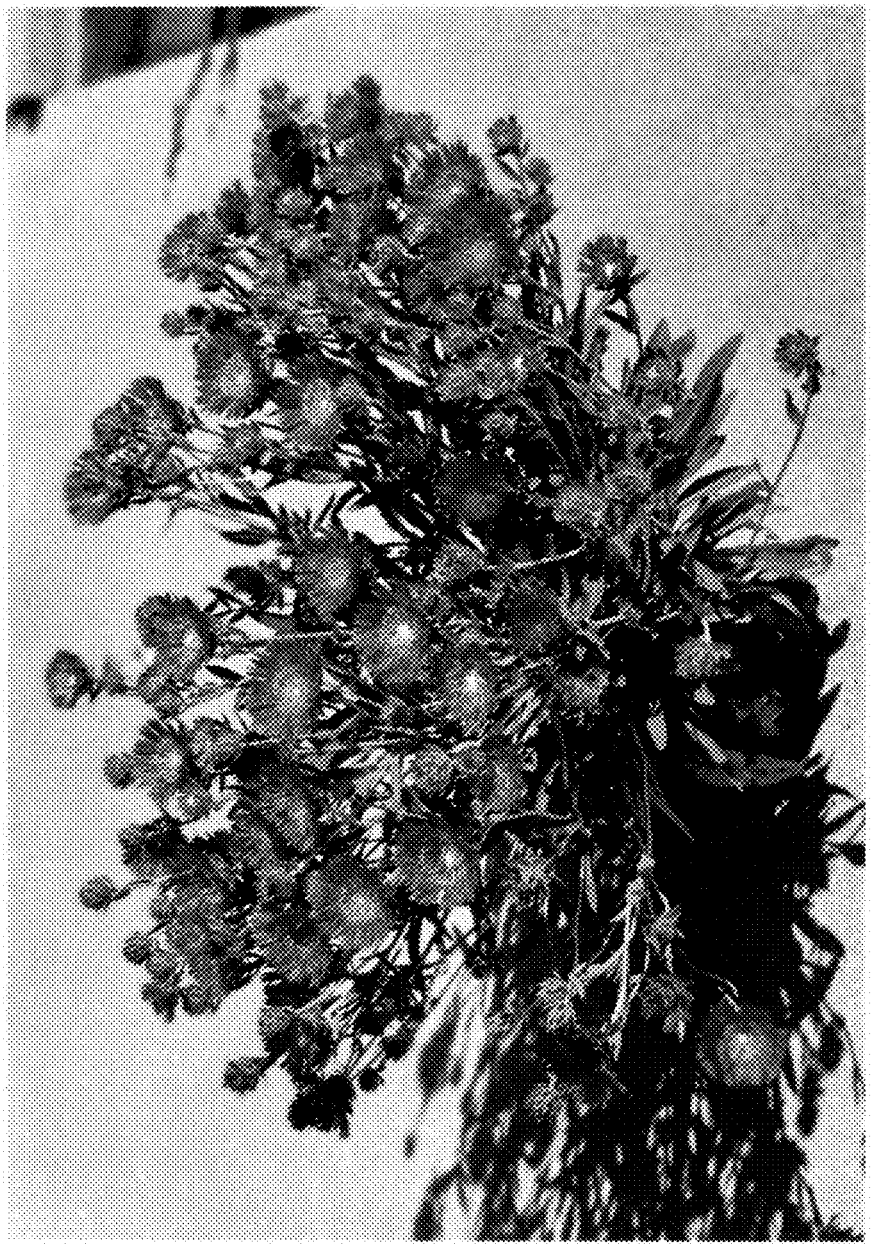

Latin name of the genus and species: *Stokesia laevis*.
Variety denomination: 'STAM01'.

BACKGROUND OF THE INVENTION

The new *Stokesia* cultivar is a product of a planned breeding program conducted by the inventor. The objective of the breeding program was to produce floriferous new *Stokesia* varieties with strong stems, large flowers with intense color and floriferous plants. The crossing resulting in this new variety was made during 2016, at a nursery in Gwangju-si, South Korea.

The seed parent is an unpatented, propriety variety of *Stokesia laevis*. The pollen parent is a different unpatented, propriety variety of *Stokesia laevis*. The new variety was selected in 2018 by the inventor in a group of seedlings resulting from the 2016 crossing, at the same nursery in Gwangju-si, South Korea.

Asexual reproduction of the new cultivar 'STAM01' was first performed by vegetative cuttings during 2018, in Gwangju-si, South Korea. Subsequent propagation has shown that the unique features of this cultivar are stable and reproduced true to type in multiple successive generations.

SUMMARY OF THE INVENTION

The cultivar 'STAM01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'STAM01'. These characteristics in combination distinguish 'STAM01' as a new and distinct *Stokesia* cultivar:

1. Sturdy, thick stems.
2. Floriferous plants.

3. Dense foliage.
4. Large flowers.

PARENT COMPARISON

Plants of the new cultivar 'STAM01' are similar to plants of the seed parent, in most horticultural characteristics, however, plants of the new cultivar 'STAM01' differ in the following;

1. Plants of the new variety are not as floriferous as plants of the seed parent. Plants of 'STAM01' produces branches with an average of 10 flowers; branches of the seed parents have 3 to 4 flowers.
2. The new variety produces stronger stems than stems of the seed parent which tend to lodge.
3. Stems of the new variety are thicker than stems of the seed parent.

Plants of the new cultivar 'STAM01' are similar to plants of the pollen parent, in most horticultural characteristics, however, plants of the new cultivar 'STAM01' differ in the following;

1. Flowers of the new variety are Violet-Blue; flowers of the pollen parent are white.

COMMERCIAL COMPARISON

Plants of the new cultivar 'STAM01' can be compared to the commercial variety *Stokesia* 'Purple Parasols', U.S. Plant Pat. No. 10,660. These varieties are similar in most horticultural characteristics; however, 'STAM01' differs in the following:

1. Plants of the new variety are on average 70 cm in height; plants of this comparator grown under similar conditions are 30 cm in height.
2. Flower stems of the new variety are stronger than flower stems of this comparator.
3. Ray floret length of the new variety is on average 4.2 cm; ray floret length of this comparator is on average 2 cm.

Plants of the new cultivar 'STAM01' can also be compared to the commercial variety *Stokesia* 'Purple Pixie', U.S. Plant Pat. No. 19,833. These varieties are similar in most horticultural characteristics; however, 'STAM01' differs in the following:

1. Plants of the new variety are on average 70 cm in height; plants of this comparator are 24 cm in height.
2. Plant width of the new variety is on average 75 cm; average plant width of this comparator is 35 cm.
3. Plants of the new variety produce approximately twice as many flowers as plants of this comparator.

BRIEF DESCRIPTION OF THE PHOTOGRAPHS

The accompanying photograph in FIG. 1 illustrates in full color a typical plant of 'STAM01' grown in a greenhouse in Lier, Belgium.

Figure 2:
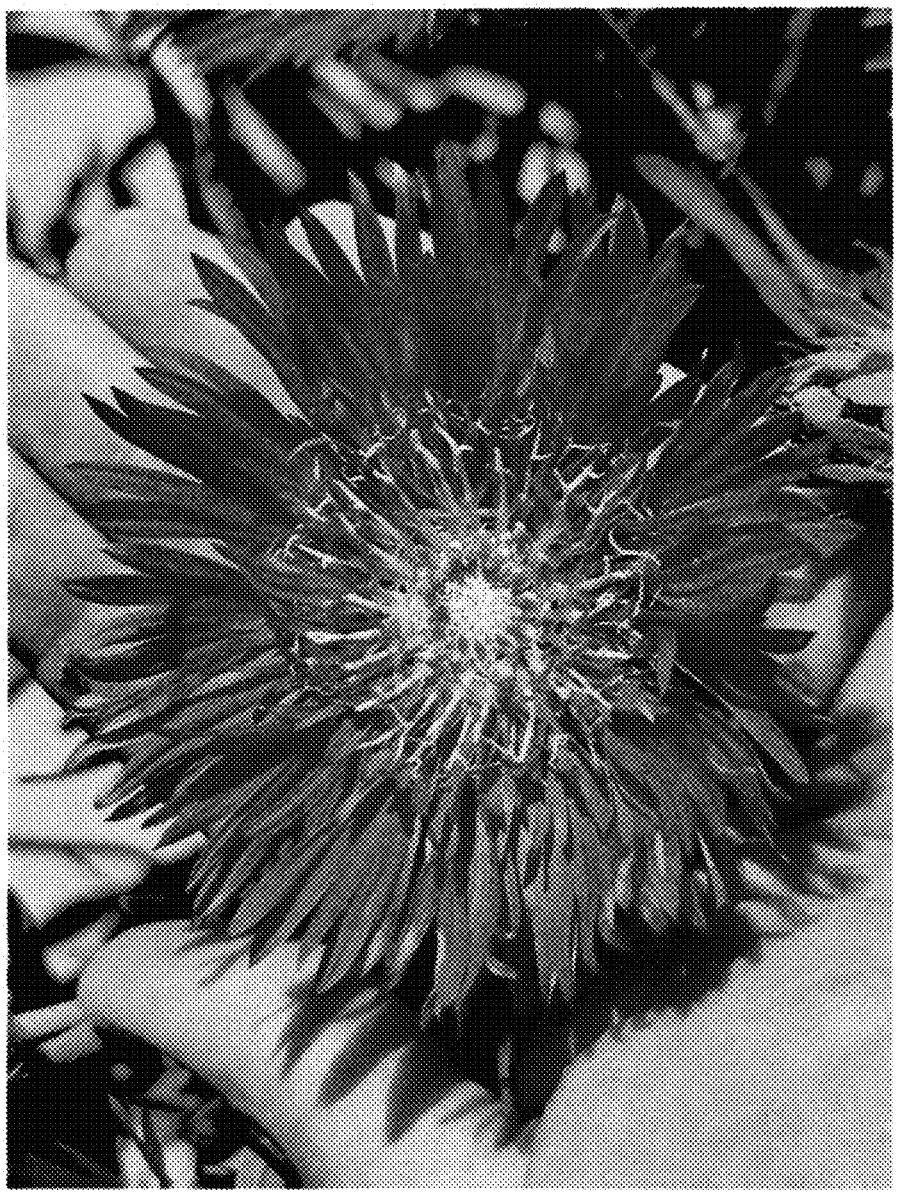

FIG. 2 illustrates in full color a typical inflorescence of 'STAM01'.

Photos are of plants of approximately 18 months of age. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'STAM01' plants grown outdoors in Lier, Belgium, under natural lighting. The plants were approximately 18 months old. The growing temperature ranged from approximately 5° C. to 30° C. during the days, 1° C. to 15° C. during the nights. Measurements and numerical values represent averages of typical plant types.

Botanical classification: *Stokesia laevis* 'STAM01'.

PROPAGATION

Typical method: Tissue culture.

Time to produce a rooted young plant: 4 to 6 weeks from stage 3 tissue culture.

Time to flowering: About 20 weeks from rooted young plant to a flowering plant in a 19 cm pot.

PLANT

Plant type: Herbaceous perennial.

Growth habit: Low, mounded.

Height: 70 cm.

Plant spread: 75 cm.

Growth rate: Vigorous.

Stem:

- *Branching*.—Free branching from the base, each main stem has 6 to 10 flowering side branches.
- *Length*.—Average 60 to 70 cm.
- *Diameter*.—8 mm.
- *Shape*.—Cylindrical.
- *Color*.—Near RHS Yellow-Green 144C.
- *Texture*.—Glabrous.
- *Strength*.—Strong.

Internode length: Up to 2.2 cm.

FOLIAGE:

Leaf:

- *Arrangement*.—Alternate or basal rosette.
- *Quantity per main stem*.—Average 12.
- *Length*.—Average 23 cm.
- *Width*.—Average 3 cm.
- *Shape*.—Oblong to lanceolate.
- *Apex*.—Acute.
- *Base*.—Attenuate.
- *Margin*.—Entire.
- *Texture*.—Glabrous all surfaces.
- *Color*.—Young foliage: Upper side: RHS Yellow-Green 146B. Under side: RHS Yellow-Green 146B and 146C. Mature foliage: Upper side: RHS Green 137C. Under side: RHS Green 137C and 137D.
- *Venation*.—Type: Pinnate. Color, upper side: RHS Yellow-Green 144B. Color, under side: RHS Yellow-Green 144B.
- *Petiole*.—Length: 5 cm. Width: 6 mm. Texture: Glabrous. Color, upper side: RHS Yellow-Green 144B. Color, under side: RHS Yellow-Green 144c.

FLOWER

Natural flowering season: Early June to September.

Flower/inflorescence type: Composite capitula.

Quantity of flowers per plant: Average 62 flowers and buds in July at one time on a 1.5 year old plant.

Flower arrangement: Outer whorl of ray florets arranged around a central disc of inner florets.

Inflorescence size:

- *Diameter*.—9 cm.
- *Depth*.—3 cm.

Persistence: Persistent.

Fragrance: None.

Bud:

- *Shape*.—Globular.
- *Length*.—2.2 cm.
- *Diameter*.—2.1 cm.
- *Color*.—RHS Yellow-Green 145A.

Outer ray florets:

- *Quantity*.—Average 24.
- *Length*.—Average 4.2 cm.
- *Width*.—1.7 cm.
- *Shape*.—Lanceolate.
- *Margin*.—Entire.
- *Apex*.—Acute.
- *Base*.—Attenuate.
- *Texture*.—Glabrous.
- *Color*.—Immature Upper surface: Near RHS Violet-Blue 93B, base Violet 86B. Immature Lower surface: Near RHS Violet-Blue 93B. Mature Upper surface: Near RHS Violet-Blue 93C, base Violet 86B. Mature Lower surface: Near RHS Violet-Blue 93C and 93D.

Inner florets/disc:
*Quantity*.—Average 120.
*Shape*.—Tubular.
*Margin*.—Entire.
*Apex*.—Acute.
*Length*.—1.9 cm.
*Width*.—9 mm.
*Base*.—Fused.
*Texture*.—Glabrous all surfaces.
*Color*.—Inner surface: Near RHS Violet-Blue 93B, base Violet 86B. Outer surface: Near RHS Violet-Blue 93B.

Involucral bracts:
*Quantity*.—Average range 50 o 60.
*Arrangement*.—Rotate.
*Shape*.—Lanceolate.
*Length*.—2.6 cm.
*Width*.—9 mm.
*Apex*.—Acute.
*Base*.—Cuneate.
*Margin*.—Serrate.
*Texture*.—Glabrous all surfaces.
*Color*.—RHS Green N137C; base and Yellow-Green 144C.

Peduncle:
*Shape*.—Round.
*Length*.—4 to 14 cm.
*Diameter*.—2.3 cm.
*Texture*.—Glabrous.
*Color*.—Near RHS Yellow-Green 144C.
*Strength*.—Strong.

REPRODUCTIVE ORGANS

Androecium present in disc florets only.

Stamens:
*Number*.—5.
*Filament length*.—Approximately 6 mm.
*Filament color*.—RHS White N155D.

Anthers:
*Length*.—Approximately 3 mm.
*Pollen color*.—RHS White N155D.

Pistil:
*Number*.—1.
*Length*.—1.8 cm.
*Style*.—Length: Approximately 1.6 cm. Color: RHS White N155D.
*Stigma*.—Shape: Cleft. Size: Approximately 0.5 mm. Color: RHS White N155D.
*Ovary*.—Minute, too small to measure or determine color.

OTHER CHARACTERISTICS

Seeds and fruits: Not observed.

Disease/pest resistance: Neither resistance nor susceptibility to normal diseases and pests of *Stokesia* has been observed.

Temperature tolerance: Cold hardy to −20° C.

What is claimed is:

1. A new and distinct cultivar of *Stokesia* plant named 'STAM01' as herein illustrated and described.

* * * * *